(12) United States Patent
Doi et al.

(10) Patent No.: US 9,376,671 B2
(45) Date of Patent: Jun. 28, 2016

(54) **METHOD OF MAKING PROTEASE THAT DECOMPOSES PROTEINS RECALCITRANT TO PROTEOLYSIS WITH *STREPTOMYCES***

(71) Applicant: MICROBIAL CHEMISTRY RESEARCH FOUNDATION, Tokyo (JP)

(72) Inventors: Hiroyasu Doi, Tokyo (JP); Naoko Kinoshita, Kanagawa (JP); Tatsuzo Oka, Kagoshima (JP); Zhao Hui, Kagoshima (JP)

(73) Assignee: MICROBIAL CHEMISTRY RESEARCH FOUNDATION, Tokyo (JP)

( * ) Notice: Subject to any disclaimer, the term of this patent is extended or adjusted under 35 U.S.C. 154(b) by 236 days.

(21) Appl. No.: 14/296,511

(22) Filed: Jun. 5, 2014

(65) Prior Publication Data

US 2014/0335595 A1 Nov. 13, 2014

Related U.S. Application Data

(60) Division of application No. 13/206,118, filed on Aug. 9, 2011, now Pat. No. 8,765,441, which is a division of application No. 12/010,010, filed on Jan. 18, 2008, now Pat. No. 8,058,026, which is a continuation of application No. 10/747,040, filed on Dec. 30, 2003, now Pat. No. 7,344,875.

(30) Foreign Application Priority Data

Jul. 1, 2003 (JP) .................................. 2003-270084

(51) Int. Cl.
*C12N 1/20* (2006.01)
*C12N 9/52* (2006.01)
*C12R 1/465* (2006.01)

(52) U.S. Cl.
CPC .. *C12N 9/52* (2013.01); *C12R 1/465* (2013.01)

(58) Field of Classification Search
None
See application file for complete search history.

(56) References Cited

FOREIGN PATENT DOCUMENTS

| JP | 753106 | 6/1995 |
|----|--------|--------|
| JP | 11-75765 | 3/1999 |
| JP | 11-292790 | 10/1999 |
| JP | 2001-37474 | 2/2001 |
| WO | WO 00/61711 | 10/2000 |

OTHER PUBLICATIONS

Oka, et al. The Journal of Biological Chemistry, Dec. 15, 1995, vol. 270, No. 50, pp. 30060-30067.
Oka, Biosciene & Industry, 2000, vol. 58, No. 5, pp. 319-324.
Yum, et al., Biosci. Biotech. Biochem, 1994, vol. 58, No. 3, pp. 470-474.
Letorneau, et al., Letter Applied Microbiology, 1998, vol. 26, pp. 77-80.
Noval et al., J. Bacteriol, 1959, vol. 77, No. 3, pp. 251-263.
Bockle, et al., Appl. And Environm. Microbiol., Oct. 1995, vol. 61, pp. 3705-3710.
Bressollier et al. App. and Environm. Microbiol., 1995, vol. 65, pp. 2570-2576.
Al-Sane, et al., Kuwait J. Sci. Eng., 2002, vol. 29, No. 2, pp. 125-138.
Burtt et al., Abstracts for the Third North American Ornithological Conference a Joint Gathering of the AOU, SCO/SOC, COS, RRF, SCSCO, CIPAMEX meeting, Sep. 24-28, 2002 in New Orleans, Louisiana # S020.
Mitsuiki et al., Biosci Biotechnol Biochem. Jan. 2002; 66(1):167-7.
Karadjova et al, Compt. Rend. Bulg. Acad. Sci. 23 (1970): 431-434.

*Primary Examiner* — Irene Marx
(74) *Attorney, Agent, or Firm* — Bacon & Thomas, PLLC

(57) ABSTRACT

The invention provides novel biologically pure cultures of microorganisms high in protease activity and capable of decomposing proteins recalcitrant to proteolysis as contained in garbage, waste water, organic waste liquids, industrial wastes and the like, a protease produced by such microorganisms and capable of decomposing proteins recalcitrant to proteolysis, and a method of utilizing the same. The novel culture is of a soil-derived microorganism belonging to *Streptomyces* sp., or a strain derived therefrom, which produces a protease capable of efficiently decomposing proteins recalcitrant to proteolysis as contained in waste water, organic waste liquids, industrial wastes and so forth.

3 Claims, 3 Drawing Sheets

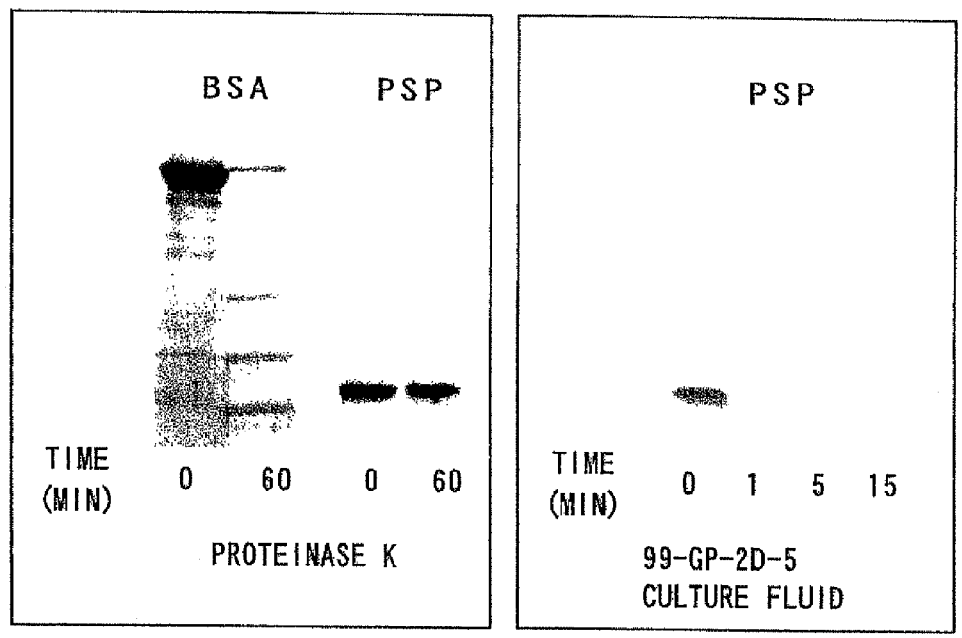

SCRAPIE

CJD

METHOD OF MAKING PROTEASE THAT DECOMPOSES PROTEINS RECALCITRANT TO PROTEOLYSIS WITH *STREPTOMYCES*

CROSS-REFERENCE TO RELATED APPLICATIONS

This application is a divisional of U.S. application Ser. No. 13/206,118 filed Aug. 9, 2011, which is a divisional of U.S. application Ser. No. 12/010,010 filed on Jan. 18, 2008, which is now U.S. Pat. No. 8,058,026 issued on Nov. 15, 2011, which is a continuation of U.S. application Ser. No. 10/747,040, filed on Dec. 30, 2003, which is now U.S. Pat. No. 7,344,875 issued on Mar. 18, 2008, which claims priority to Japanese Application No. 2003-270084 filed on Jul. 1, 2003, the entire contents of which are incorporated herein by reference.

BACKGROUND OF THE INVENTION

1. Field of the Invention

The present invention relates to a biologically pure culture of a microorganism belonging to *Streptomyces* sp. and capable of decomposing, or hydrolyzing, proteins recalcitrant to proteolysis, such as the perchloric acid-soluble protein (hereinafter referred to as "PSP"), to a method of producing a protease capable of decomposing proteins recalcitrant to proteolysis from the culture of the microorganism, to the isolated protease, to novel mutant strains of the microorganism, and to a method of treating materials containing proteins recalcitrant to proteolysis using the protease.

2. Description of the Prior Art

The technology of decomposing, or degrading, various proteins into peptides or amino acids is widely used in various industries, for example in producing preparations for medical use and food materials. The method of chemically decomposing proteins using hydrochloric acid or the like has excellent decomposition efficiency but may cause environmental pollution or the formation of undesirable byproducts due to severe decomposition conditions. Therefore, in human-related industries, in particular, methods of decomposition by means of proteases are utilized (cf. e.g. Japanese Patent Publication (JP Kokoku) H07-53106 and Laid-open Japanese Patent Application (JP Kokai) H11-75765). Thus, known in the art are compositions containing a *Bacillus subtilis*-derived enzyme which is thermostable in the middle to high temperature range and at the same time capable of depolymerizing proteins and can effectively decompose proteins normally recalcitrant to proteolysis (cf. e.g. Laid-open Japanese Patent Application (JP Kokai) 2001-037474), and proteolytic detergent compositions containing a *Pyrococcus* strain-derived superthermostable protease and excellent in detergency against proteinaceous stain components (cf. e.g. WO 00/61711).

The present inventors discovered a protein extractable from a hepatic cytoplasmic fraction with perchloric acid and having protein synthesis inhibiting activity, also referred to as "perchloric acid—soluble protein" or "PSP" (cf. e.g. J. Biol. Chem., 270, 30060, 1995). As a result of their continued study, they found that the inhibition of PSP expression results in cell proliferation. Further, they found that, when PSP is applied to proximal renal tubule cells, the intracellular expression of PSP is inhibited and, as a result, the proliferation of renal tubule cells is promoted, and thus PSP is effective in the treatment of nephropathies (cf. e.g. Laid-open Japanese Patent Application (JP Kokai) H11-292790). It is also known that PSP is structurally similar to those proteins called "abnormal prions" which cause BSE (bovine spongiform encephalopathy) and the like, is hardly decomposed and is preserved in various organisms, from animals to prokaryotes, and occurs universally in the environment (cf. e.g. Bioscience and Industry, 58 17-22, 2000).

Further, it has been reported that SAP, an extracellular alkaline serine protease, produced by *Streptomyces* sp. YSA-130 and homogeneously purified by CM-Sephadex column chromatography and crystallization, is a monomeric protein with a molecular weight of 19,000 (as determined by SDS-PAGE and gel filtration), that the amino acid composition and N-terminal sequence of SAP are very similar to those of other bacterial serine proteases such as *Streptomyces griseus* protease A and B, *Lysobacter* enzymogenes-derived .alpha.-soluble protease, and *Nocardiopsis dassonvillei* subsp. *prasina* OPC-210-derived alkaline serine protease NDP-I, that the optimum temperature and optimum pH for SAP are 60.° C. C. and pH 11.5, respectively, and that SAP is stable at temperatures up to 50.° C. C. and at pH 4 to 12, and that the activity of SAP is inhibited by $Ag.sup.+$, $Hg.sup.+$, $Co.sup.2+$, sodium dodecyl sulfate, N-bromosuccinimide, diisopropyl fluorophosphate (DFP), 2,3-butanedione, 5,5'-dithiobis(2-nitrobenzoic acid) (DTNB), iodoacetic acid, N-ethylmaleimide (NEM), phenylmethanesulfonyl fluoride (PMSF) and phenylglyoxal (cf. e.g. Biosci. Biotech. Biochem., 58 (3), 470-474, 1994).

In recent years, a large number of microorganisms showing protease activity have been isolated from soils and biotic sludge. However, it has been considered that the utilization of these microorganisms cannot succeed in completely decomposing proteinaceous components, in particular proteinaceous components recalcitrant to proteolysis, contained in garbage, waste water, organic waste liquids, industrial wastes and the like. Accordingly, it is an object of the present invention to provide a novel microorganism high in protease activity and capable of decomposing proteins recalcitrant to proteolysis as contained in garbage, waste water, organic waste liquids, industrial wastes and the like, a protease produced by such microorganism and capable of decomposing proteins recalcitrant to proteolysis, and a method of utilizing the same.

SUMMARY OF THE INVENTION

The present invention relates to a microorganism belonging to *Streptomyces* sp. and having the capability of efficiently decomposing proteins recalcitrant to proteolysis as contained in waste water, organic waste liquids, industrial wastes and the like, and selected from a large number of soil microorganisms on the basis of high protease activity. A protease produced by the microorganism can decompose the hardly degradable PSP and abnormal prion proteins, such as the one causing BSE.

Thus, the invention provides a biologically pure culture of the bacterial strain *Streptomyces* sp. 99-GP-2-D-5 (FERM P-19336) capable of producing a protease decomposing protein recalcitrant to proteolysis and microbial strains derived therefrom.

In another aspect, the present invention provides a biologically pure culture of a microorganism belonging to *Streptomyces* sp. and capable of producing a protease decomposing protein recalcitrant to proteolysis, and having the following bacteriological characteristics A to C: A. Morphological characteristics;

(1) A relatively long, wavy aerial mycelium extends from the branched substrate mycelium and, rarely, it shows a hook-like or loop-like shape;

(2) Each chain of mature spores has 10 to 50 oval spores and the spore size is about 0.6 to 0.7.times.0.8 to 1.0 micron;

(3) The spore surface is smooth;

(4) Neither verticillate branching nor rhizomorph nor sporangium nor motile spore is observable; B. LL-2,6-Diaminopimelic acid is included in the cell wall composition; C. A partial base sequence (400-500 bp) of the 16S ribosome RNA gene is at least 90% homologous to those of actinomycetes belonging to the genus *Streptomyces*; and microbial strains derived therefrom.

The aforementioned microorganism belonging to *Streptomyces* sp. further has the bacteriological characteristics D: D. Growth conditions on various media:

(1) Yeast-malt-agar medium (ISP medium 2, cultivation at 27.° C. C.): a small number of gray white [1 dc, Putty] to light olive gray [11/2 ge, Lt Olive Gray] aerial mycelia are adherent to the light yellow [2 ea, Lt Wheat] growth, and no soluble pigment is observable;

(2) Oatmeal-agar medium (ISP medium 3, cultivation at 27.° C. C.): a small number of white aerial mycelia are adherent to the colorless to pale yellow [11/2 ca, Cream] growth, and no soluble pigment is observable;

(3) Starch-inorganic salt-agar medium (ISP medium 4, cultivation at 27.° C. C.): a small number of white aerial mycelia are adherent to the colorless growth, and no soluble pigment is observable;

(4) Glycerol-asparagine-agar medium (ISP medium 5, cultivation at 27.° C. C.): the growth is colorless, no aerial mycelia are adherent, and no soluble pigment is observable; and (5) Sucrose-nitrate-agar medium (cultivation at 27.° C. C.): White mycelia are adherent thinly to the white growth, and no soluble pigment is observable.

The present invention also provides a protease capable of decomposing proteins recalcitrant to proteolysis which is obtained by cultivating the strain *Streptomyces* sp. 99-GP-2-D-5 (FERM P-19336) and which protease can decompose the perchloric acid-soluble protein PSP and/or abnormal prion proteins, which decomposition has an optimum pH of 9 to 12 and an optimum temperature of 60-70.° C. C.;

The protease capable of decomposing proteins recalcitrant to proteolysis of the present invention preferably has a N terminus with an amino acid sequence given as SEQ. I.D. NO.: 1.

The proteins recalcitrant to proteolysis (degraded by the protease of the present invention) include the perchloric acid-soluble protein PSP and abnormal prion proteins.

The present invention also provides a method of producing a protease capable of decomposing proteins recalcitrant to proteolysis, which method comprises cultivating a microorganism selected from the group consisting of *Streptomyces* (SP 99-GP-2-D4 FERM P-19336)) and microbial strains derived therefrom, in a culture medium, the microorganism producing the protease as an extracellular product in the culture medium, and isolating the protease from the culture medium. The aforementioned microorganisms produce the subject protease in recoverable amounts. Optionally, the protease is purified after isolation. However, the culture medium per se, containing the protease, may be used for protein degradation.

Thus, the present invention further provides an agent for decomposing proteins recalcitrant to proteolysis which comprises, as an active ingredient, the culture medium of the microorganism deposited as FERM P-19336 (or microorganism derived therefrom). Alternatively, the active ingredient is the protease isolated as an extracellular product of the microorganism and which decomposes proteins recalcitrant to proteolysis.

It follows that the present invention also provides a method of treating materials containing proteins recalcitrant to proteolysis which method comprises applying the aforementioned protease or decomposing agent containing same to those materials containing the proteins recalcitrant to proteolysis.

The *Streptomyces* sp. 99-GP-2-D-5 strain and microorganisms derived therefrom have high protease activity and, therefore, can completely decompose protein components otherwise highly resistant to degradation and contained in garbage, waste water, organic waste liquids, industrial wastes and so on, and thus can markedly reduce the quantity of residues produced.

The present invention also provides artificially produced mutant strains of *Streptomyces* sp. 99-GP-2-D-5 (FERM P-19336), which mutant strains likewise produce recoverable amounts of the aforementioned protease which decompose proteins otherwise recalcitrant to proteolysis.

The proteins normally recalcitrant to proteolysis, but susceptible to decomposition by the protease of the present invention, include the perchloric acid-soluble protein PSP and abnormal prion proteins.

BRIEF DESCRIPTION OF THE DRAWINGS

FIGS. 1A and 1B illustrate the high level of protease activity of the microorganism according to the invention, namely the *Streptomyces* sp. 99-GP-2-D-5 strain, against the degradation-resistant protein PSP.

FIG. 1A (right) shows SDS-polyacrylamide electrophoretograms respectively obtained after 0, 1, 5 and 15 minutes of reaction, at 37.° C. C., of 20 .mu.l of a culture of *Streptomyces* sp. 99-GP-2-D-5 with PSP.

FIG. 1B (left) shows SDS-polyacrylamide electrophoretograms obtained after 0 or 60 minutes of reaction, at 37.° C. C., of proteinase K, a known protease, with BSA or PSP.

FIG. 2A (right) shows SDS-polyacrylamide electrophoretograms respectively obtained after 60 minutes of reaction, at 37.° C. C., of 20 .mu.l or 40 .mu.l of a culture of *Streptomyces* sp. 99-GP-2-D-5 or 2 .mu.g, 4 .mu.g or 10 .mu.g/20 .mu.l of proteinase K, a known protease, with the Creutzfeldt-Jakob disease-derived abnormal prion protein (CJD).

FIG. 2B (left) shows SDS-polyacrylamide electrophoretograms obtained after 60 minutes of reaction, at 37.° C. C., of 20 .mu.l or 40 .mu.l of a culture of *Streptomyces* sp. 99-GP-2-D-5 or 2 .mu.g, 4 .mu.g or 10 .mu.g/20 .mu.l of proteinase K, a known protease, with the scrapie-derived abnormal prion protein.

DETAILED DESCRIPTION OF THE PREFERRED EMBODIMENTS

Figure 2B:
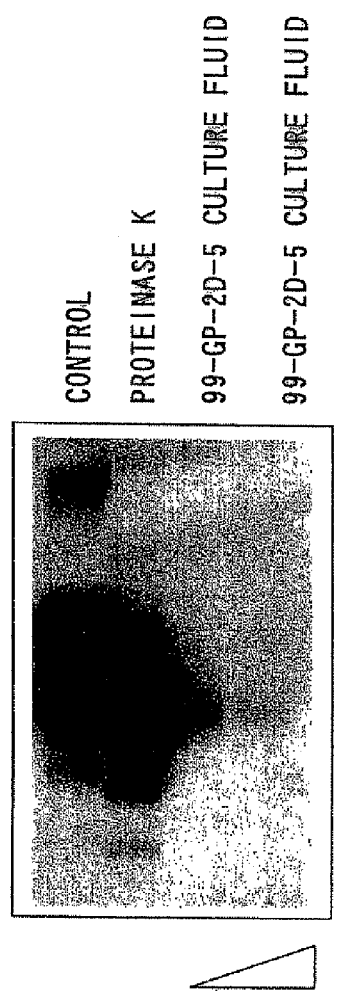
FIGS. 2A and 2B illustrate the high protease activity of the microorganism according to the invention, namely the *Streptomyces* sp. 99-GP-2-D-5 strain, against abnormal prions which are degradation-resistant proteins, also referred to herein as "proteins recalcitrant to proteolysis."

The microorganisms of the present invention, include the *Streptomyces* sp. 99-GP-2-D-5 strain (FERM P-19336) which produces, as an extracellular product, a protease capable of decomposing proteins recalcitrant to proteolysis, and microorganisms belonging to *Streptomyces* sp. which produce, as an extracellular product, a protease capable of decomposing proteins recalcitrant to proteolysis and which have the bacteriological characteristics A to C, preferably A to D, given below (hereinafter such microorganisms are collectively referred to as "99-GP-2-D-5 and equivalent strains"), and microbial strains derived therefrom, without any further restriction. The term "protease capable of decomposing proteins recalcitrant to proteolysis" means a protease capable of decomposing those proteins which are known in the art and previously regarded in the art as recalcitrant to proteolysis, such as PSP and abnormal prion proteins. Preferably, as used herein, the terminology refers to a protease which, when subjected to a proteolytic test comprising mixing 20 .mu.l (0.6 mg/ml) of the swine liver-derived protein PSP with 20 .mu.l of a microbial culture and judging, after 60 minutes, preferably 20 minutes, more preferably 5 minutes, of reaction at 37.° C. C., the protease activity based on the disappearance of the PSP band upon SDS-PAGE, causes the disappearance of the PSP band.

A. Morphological Characteristics (1) A relatively long, wavy aerial mycelium extends from the branched substrate mycelium and, rarely, it shows a hook-like or loop-like shape;

(2) Each chain of mature spores is a chain of 10 to 50 oval spores and the spore size is about 0.6 to 0.7.times.0.8 to 1.0 micron;

(3) The spore surface is smooth;

(4) Neither verticillate branching nor rhizomorph nor sporangium nor motile spore is observable;

B. LL-2,6-Diaminopimelic acid is included in the cell wall composition;

C. A partial base sequence (400-500 bp) of the 16S ribosome RNA gene is at least 90%, preferably 95% or more, homologous to those of actinomycetes belonging to the genus *Streptomyces*;

D. Growth conditions on various media:

(1) Yeast-malt-agar medium (ISP medium 2, cultivation at 27.° C. C.): a small number of gray white [1 dc, Putty] to light olive gray [11/2 ge, Lt Olive Gray] aerial mycelia are adherent to the light yellow [2 ea, Lt Wheat] growth, and no soluble pigment is observable;

(2) Oatmeal-agar medium (ISP medium 3, cultivation at 27.° C. C.): a small number of white aerial mycelia are adherent to the colorless to pale yellow [11/2 ca, Cream] growth, and no soluble pigment is observable;

(3) Starch-inorganic salt-agar medium (ISP medium 4, cultivation at 27.° C. C.): a small number of white aerial mycelia are adherent to the colorless growth, and no soluble pigment is observable;

(4) Glycerol-asparagine-agar medium (ISP medium 5, cultivation at 27.° C. C.): the growth is colorless, no aerial mycelia are adherent, and no soluble pigment is observable;

(5) Sucrose-nitrate-agar medium (cultivation at 27.° C. C.): White mycelia are adherent thinly to the white growth, and no soluble pigment is observable.

The microbial strains derived from the 99-GP-2-D-5 and equivalent strains of the invention include offspring of the 99-GP-2-D-5 and equivalent strains and artificial or spontaneous mutants of the 99-GP-2-D-5 and equivalent strains, provided that they are capable of producing a protease capable of decomposing proteins recalcitrant to proteolysis. Such strains belonging to the genus *Streptomyces*, inclusive of the 99-GP-2-D-5 and equivalent strains, like other strains of the genus *Streptomyces*, are subject to changes in their characteristics and can be readily mutated by such artificial means of mutation as the use of ultraviolet rays, X rays, or chemical agents, and all such artificial mutants that can produce a protease capable of decomposing proteins recalcitrant to proteolysis fall within the scope of the present invention.

For the artificial cultivation of the 99-GP-2-D-5 and equivalent strains of the invention or strains derived therefrom, any of the strains of the invention is aerobically cultivated on a medium containing nutrients capable of being utilized by actinomycetes. Usable as the nutrient sources are those medium components which are known in the art and have been utilized in cultivating actinomycetes. Thus, for example, glucose, potato starch, dextrin and the like can be used singly or in combination as the carbon sources, and yeast extract, Tryptose, corn steep liquor, soybean flour, meat extract, tomato puree and the like can be used singly or in combination as the inorganic and organic nitrogen sources. Where necessary, inorganic salts such as sodium chloride, calcium carbonate, magnesium sulfate, copper sulfate, iron sulfate, zinc sulfate, manganese chloride, cobalt chloride and phosphate salts may be added each in an appropriate amount and, further, organic materials, for example amino acids, vitamins and nucleic acids, and inorganic materials may be added each in an appropriate amount. These nutrient sources may be of any kind provided that they can be utilized by the microbial strain of the invention. Thus, all the materials known in the art for the cultivation of actinomycetes can be utilized.

The method of cultivation is not particularly restricted but the liquid culture method, in particular the shake culture method, may be mentioned as a preferred example. The cultivation is desirably carried out at a temperature of 20 to 40.° C. C. and at a weakly acidic to alkaline pH. In the case of liquid culture, 4 to 6 days of cultivation generally results in protease formation and accumulation in the culture fluid. After accumulation of the maximum amount of the product in the culture fluid, the cultivation is terminated, and cells are separated from the culture fluid by filtration. The culture liquid as is can be used as a protease-containing material, i.e., as the active agent of the present invention.

The degradation-resistant protein-decomposing protease of the invention is not particularly restricted but includes the protease which is obtained by cultivating the *Streptomyces* sp. 99-GP-2-D-5 strain (FERM P-19336) and is capable of decomposing at least one, preferably both, of PSP and abnormal prion proteins, which decomposing has an optimum pH at 9 to 12 and an optimum temperature at 60-70.° C. C., and equivalents thereto. A preferred example is a protease whose N-terminal amino acid sequence is YDLVGGDAYYIG (SEQ. I.D. NO.: 1). The terminology "capable of decomposing PSP" as used herein means that the protease in question, when subjected to a proteolytic test comprising mixing 10 .mu.l (0.6 mg/ml) of the swine liver-derived protein PSP with 10 .mu.l (0.6 mg/ml) of the protease and judging, after 60 minutes, preferably 20 minutes, more preferably 5 minutes, of reaction at 37.° C. C., the protease activity based on the disappearance of the PSP band upon SDS-PAGE, causes the disappearance of the PSP band. The terminology "capable of decomposing abnormal prion proteins" so referred to herein means that the protease in question, when subjected to a proteolytic test comprising mixing 20 .mu.l (3 mg/ml) of the Creutzfeldt-Jakob disease- or scrapie-derived abnormal prion protein with 20 .mu.l (0.6 mg/ml) of a protease-containing culture fluid and judging, after 60 minutes, preferably 20 minutes, more preferably 5 minutes, of reaction at 37.° C. C., the protease activity based on the disappearance of the abnormal prion protein band upon western blotting, causes the disappearance of the abnormal prion protein band.

The degradation-resistant protein-decomposing protease of the invention can be obtained, for example, by cultivating the 99-GP-2-D-5 strain or an equivalent thereof or a transformant microorganism constructed in the conventional manner based on the base sequence information for the degradation-resistant protein-decomposing protease, and isolating and purifying the protease from the culture fluid in the conventional manner. For the purification from the culture fluid, use can be made of such techniques as precipitation with ammonium sulfate or ethanol, acid extraction, anion or cation exchange chromatography, phosphocellulose chromatography, hydrophobic interaction chromatography, affinity chromatography, hydroxyapatite chromatography and lectin chromatography, preferably high-performance liquid chromatography. In the case of affinity chromatography, in particular, the degradation-resistant protein-decomposing protease of the invention can be recovered by using, as the affinity column, a column resulting from binding of an antibody, for example a monoclonal antibody, against the degradation-resistant protein-decomposing protease of the invention or, in case of addition of an ordinary peptide tag to the degradation-resistant protein-decomposing protease of the invention, a column prepared by binding a substance having affinity for the peptide tag.

The method of producing the degradation-resistant protein-decomposing protease of the invention may be any of those comprising cultivating, in a medium, a microorganism belonging to the genus *Streptomyces* and capable of producing the degradation-resistant protein-decomposing protease of the invention, and recovering the degradation-resistant protein-decomposing protease of the invention from the culture. As preferred examples of the microorganism belonging the genus *Streptomyces* and capable of producing the degradation-resistant protein-decomposing protease of the invention, there may be mentioned the 99-GP-2-D-5 and equivalent strains.

The degradation-resistant protein-decomposing agents of the present invention are not particularly restricted but include those containing the culture of the 99-GP-2-D-5 strain or an equivalent thereto or a strain derived therefrom or the degradation-resistant protein-decomposing protease of the invention as an active ingredient. The method of treating materials containing degradation-resistant proteins according to the invention is not particularly restricted but may be any of the methods comprising applying the degradation-resistant protein-decomposing agent of the invention to the materials containing degradation-resistant proteins and, in particular when the microorganism of the invention is directly used for the purpose of efficiently decomposing hardly degradable proteins contained in garbage, waste water, organic waste liquids, or industrial wastes, the culture fluid containing the microorganism of the invention may be sprayed as such onto such waste materials or may be used in the form of preparations or powders prepared in the conventional manner.

The following examples illustrate the invention more specifically. They are, however, by no means limitative of the technical scope of the invention.

Example 1

Isolation of *Streptomyces* sp. 99-GP-2-D-5

One gram of a soil collected was diluted with 9 ml of deionized and sterilized water, followed by further $10^2$- fold or $10^3$-fold dilution. Then, 0.1 ml of each dilution was scattered on an agar plate made of the colloidal chitin agar medium specified below, and cultured at 27° C. Microorganisms were discriminated (differentiated) based on colony morphology, microscopic observation of microbial cells, and biochemical tests. When a mixture of a plurality of bacterial strains was obtained, this was further treated by the dilution method. In this way, a bacterial strain having the bacteriological characteristics A to D described above was obtained. Although this isolated microbial strain agreed well in various characteristics with microorganisms belonging to the genus *Streptomyces*, a partial base sequence (459 bp) of the 16S ribosome gene of the isolated microbial strain showed only 95% homology to those of the known microorganisms of the genus *Streptomyces*. Therefore, the isolated microbial strain was judged to be a previously unknown microorganism and was named *Streptomyces* sp. 99-GP-2D-5. The *Streptomyces* sp. 99-GP-2D-5 strain obtained has been deposited as of May 7, 2003 by the present applicants with the National Institute of Advanced Industrial Science and Technology International Patent Organism Depositary (Tsukuba, Japan) under the deposition/accession number FERM P-19336, now FERM BP-08594.

Composition of Colloidal Chitin Agar Medium (pH 7.0)

| | |
|---|---|
| Colloidal chitin | 2 g |
| $K_2HPO_4$ | 0.7 g |
| $KH_2PO_4$ | 0.3 g |
| $MgSO_4 \cdot 5H_2O$ | 0.5 g |
| $FeSO_4 \cdot 7H_2O$ | 0.01 g |
| $ZnSO_4$ | 0.001 g |
| $MnCl_2$ | 0.001 g |
| Agar | 20 g |
| Deionized water | 1000 ml |

The above colloidal chitin was prepared by the method described in Biseibutsu Jikken Manual (Manual for Microbiological Experiments, edited by Kyowa Hakko Kogyo Tokyo Laboratory, published 1986 by Kodansha). Thus, crude chitin (product of Wako Pure Chemical Industries) was washed with sodium hydroxide and 1 N hydrochloric acid respectively for 24 hours. After 5 repetitions of each washing, the chitin was washed four times with 95% ethanol. The thus-obtained white chitin (15 g) was placed in 100 ml of concentrated hydrochloric acid, and the mixture was stirred with ice cooling, followed by filtration through glass wool. The filtrate was poured into ice-cooled water for precipitating chitin. That portion of chitin on the glass wool was recovered by further treatment with hydrochloric acid and repetitions of the same procedure as mentioned above. The chitin-containing solution was allowed to stand overnight, then adjusted to pH 7.0 with sodium hydroxide, and chitin was recovered by centrifugation and washing.

Example 2

Degradation-Resistance Test

Figure 2A:
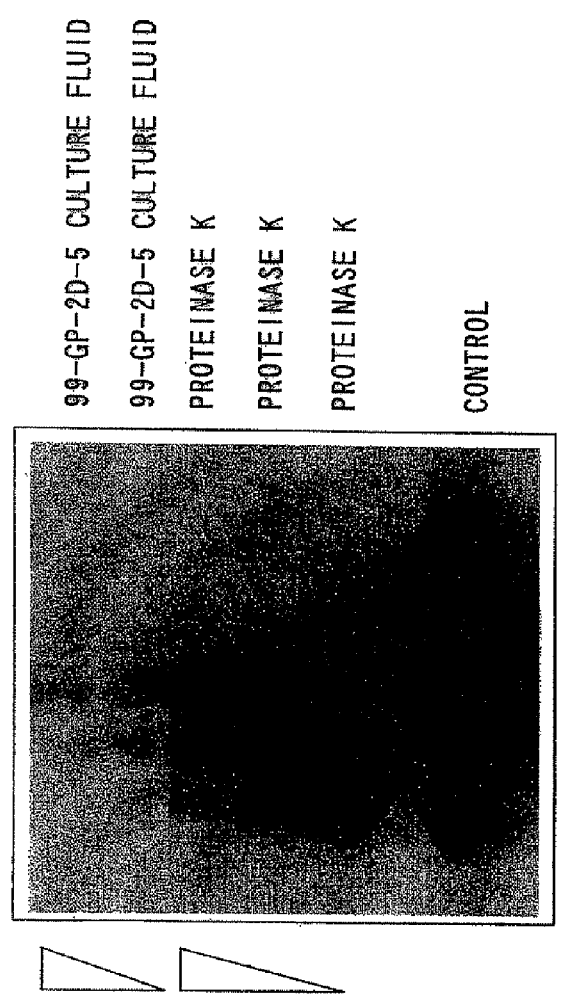

The degradation-resistant protein decomposition test was carried out using the swine liver-derived protein PSP prepared by the present inventors according to the method described in the literature (J. Biol. Chem., 270, 30060, 1995). Thus, 20 .mu.l (0.6 mg/ml) of PSP was mixed with 20 .mu.l of a culture of the *Streptomyces* sp. 99-GP-2-D-5 strain, the reaction was allowed to proceed at 37.° C. C. for 60 minutes, and then the protease activity was judged based on the disappearance of the PSP band upon SDS-PAGE. The results are shown in FIG. 1A (right). In a control run, proteinase K (product of Wako Pure Chemical Industries), a known protease in frequent use, was used, and the results obtained are shown in FIG. 1B (left). From these results, it was revealed that the 99-GP-2-D-5 strain culture fluid caused complete disappearance of the PSP band in 5 minutes after the start of the reaction, hence the 99-GP-2-D-5 strain is a strain showing a high level of decomposing ability against the degradation-resistant protein PSP and having high activity in degradation of proteins normally recalcitrant to proteolysis. On the contrary, it is evident that proteinase K can decompose BSA (bovine serum albumin, product of Sigma) at 37° C. in 60 minutes but cannot decompose PSP. In the same manner, 20 .mu.l (3 mg/ml) of an abnormal prion protein was mixed with 20 .mu.l (0.6 mg/ml) of the protease-containing culture fluid and, after 60 minutes of reaction at 37.° C. C., the protease activity was judged based on the disappearance of the abnormal prion protein band upon western blotting. The results of decomposition of the scrapie-derived abnormal prion protein are shown in FIG. 2B (left), and the results of decomposition of the Creutzfeldt-Jakob disease-derived abnormal prion protein are shown in FIG. 2A (right). From these results, it was found that the 99-GP-2-D-5 strain culture fluid caused complete disappearance of the abnormal prion protein bands in 60 minutes, hence the 99-GP-2-D-5 strain is a strain showing a high level of activity in decomposing the abnormal prion proteins. On the contrary, it is evident that proteinase K cannot decompose the abnormal prion proteins in 60 minutes at 37° C.

Example 3

Purification of the Protease

The *Streptomyces* sp. 99-GP-2-D-5 strain was cultured on SA medium at 27° C. for 5 days. Cells were removed by centrifugation, and the culture supernatant was heated at 55° C. for 1 hour to thereby decompose proteins other than the desired enzyme, the precipitate caused to form by 20% ammonium sulfate was removed, the remaining supernatant was saturated with 80% ammonium sulfate, and a roughly purified enzyme fraction was recovered by centrifugation. The roughly purified enzyme was dialyzed against 0.05 M phosphate buffer (pH 6.8), and the dialyzate was purified on a Sephadex-SP ion exchanging column. The composition of the above-mentioned SA medium is shown below.
Composition of SA Medium (pH 7.0)

| | |
|---|---|
| Meat extract (product of Kyokuto Pharmaceutical Industrial Co.) | 0.3 g |
| Tryptose (product of Difco) | 0.5 g |
| Yeast extract (product of Difco) | 0.5 g |
| Glucose (product of Wako) | 0.1 g |
| Soluble starch (product of Wako) | 2.4 g |
| CaCO$_3$ | 0.2 g |
| Deionized water | 100 ml |

Example 4

Figure 3B:
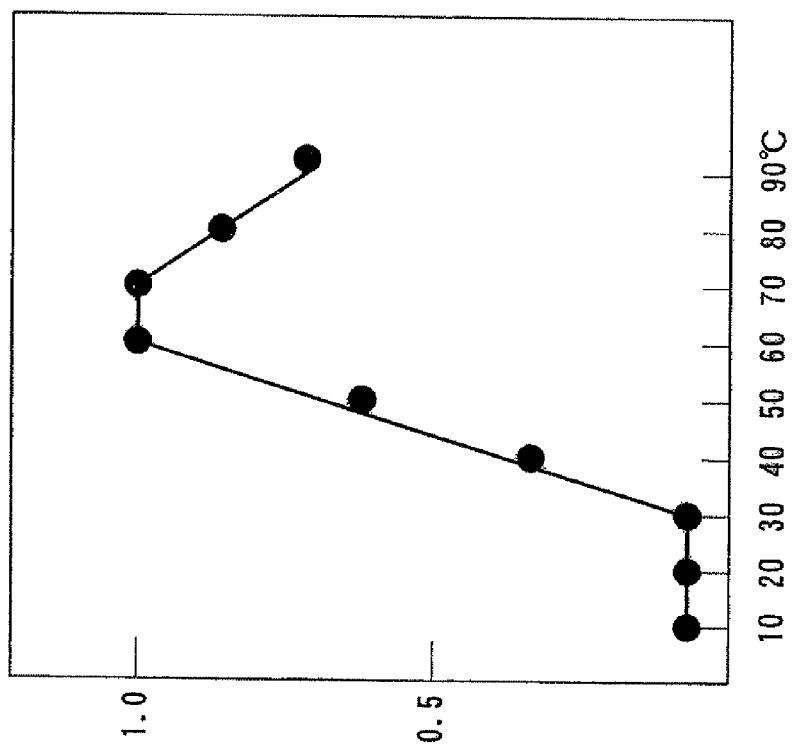
FIG. 3A (left) is a graph indicating the optimum temperature, and FIG. 3B (right) is a graph indicating the optimum pH, for the degradation-resistant protein-decomposing protease of the invention.
Figure 3A:
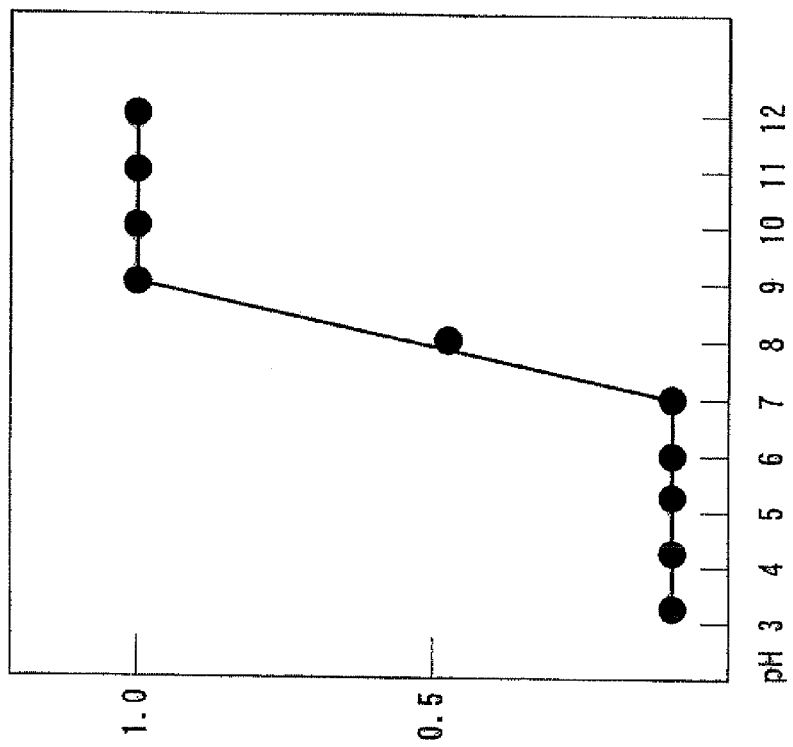

Physicochemical Properties of the Degradation-Resistant Protein-Decomposing Protease For determining the optimum temperature for the purified protease, PSP and a solution of the enzyme were added to a buffer solution with pH 11.5 to make 50-.mu.l portions of a mixture. The portions were incubated at various temperatures for 10 minutes, 2.times. sample buffer containing PMSF was added, and the mixture was heated at 100° C. for 5 minutes and then subjected to SDS-PAGE and western blotting. The bands obtained were scanned using an image analyzer (product of Fuji Photo Film Co.). For determining the optimum pH, PSP and a solution of the enzyme were added to each of buffer solutions with pH 3 to 12 to make a total amount of 50 .mu.l and, after 10 minutes of incubation at 37° C. 2 times sample buffer containing PMSF was added, and the mixture was heated at 100° for 5 minutes and then subjected to SDS-PAGE and western blotting. The bands obtained were scanned using the image analyzer. The results are shown in FIG. 3. The molecular weight of the enzyme was determined by mass spectrometry using a mass spectrograph (product of JEOL Ltd.) and found to be 19,327. The N-terminal amino acid sequence was determined by the Edman degradation method using the HP G1005A Protein Sequencing System (product of Hewlett-Packard).

The teachings of Japanese Application No. 2003-270084, filed on Jul. 1, 2003 are incorporated herein in their entirety, inclusive of the specification, claims and drawings.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of producing a protease capable of decomposing protein recalcitrant to proteolysis comprising:
   cultivating *Streptomyces* sp. 99-GP-2D-5 (FERM BP-08594) in a culture medium, and
   isolating the protease from the culture medium.

2. The method of claim 1, wherein the proteins recalcitrant to proteolysis include at least one protein selected from the group consisting of perchloric acid-soluble protein PSP, Creutzfeldt-Jakob disease-derived abnormal prion proteins and scrapie-derived abnormal prion proteins.

3. The method of claim 1, wherein the protease comprises an N terminus having the amino acid sequence Tyr Asp Leu Val Gly Asp Ala Tyr Tyr Ile Gly (SEQ I.D. NO.: 1).

\* \* \* \* \*

SEQUENCE LISTING

```
<160> NUMBER OF SEQ ID NOS: 1

<210> SEQ ID NO 1
<211> LENGTH: 12
<212> TYPE: PRT
<213> ORGANISM: Streptomyces sp.

<400> SEQUENCE: 1

Tyr Asp Leu Val Gly Gly Asp Ala Tyr Tyr Ile Gly
 1               5                   10
```